United States Patent
Aldeen

[11] Patent Number: 5,882,943
[45] Date of Patent: Mar. 16, 1999

[54] FILTRATION APPARATUS, KIT AND METHOD FOR PROCESSING PARASITE SAMPLES

[76] Inventor: William Erick Aldeen, 1357 E. 8027 South, Sandy, Utah 84093

[21] Appl. No.: 690,672

[22] Filed: Jul. 31, 1996

[51] Int. Cl.⁶ .............................. B01D 29/00; B01L 11/00
[52] U.S. Cl. .................... 436/178; 436/174; 436/175; 436/179; 422/72; 422/101; 210/323.2; 210/456; 210/787
[58] Field of Search ................ 422/68.1, 72, 101, 422/102, 103; 436/63, 174, 177, 178, 179, 180; 210/323.1, 446, 453, 456, 473, 787; 209/172, 173, 17

[56] References Cited

U.S. PATENT DOCUMENTS

| | | | |
|---|---|---|---|
| 556,598 | 9/1896 | Raybuck et al. | 422/100 |
| 3,819,045 | 6/1974 | Greenwald | 209/17 |
| 3,905,895 | 9/1975 | Addis | 209/17 |
| 3,936,373 | 2/1976 | Studer | 209/17 |
| 4,081,356 | 3/1978 | Zierdt | 209/3 |
| 4,288,316 | 9/1981 | Hennessy | 209/17 |
| 4,293,405 | 10/1981 | Greenwald | 209/17 |
| 4,406,786 | 9/1983 | Hein | 210/223 |
| 4,427,769 | 1/1984 | Addercrentz et al. | 435/7 |
| 4,678,559 | 7/1987 | Szabados | 209/17 |
| 4,956,298 | 11/1990 | Diekmann | 430/311 |
| 4,990,253 | 2/1991 | Vcelka | 210/359 |
| 5,066,463 | 11/1991 | Chang | 422/56 |
| 5,094,951 | 3/1992 | Grow et al. | 436/66 |
| 5,208,161 | 5/1993 | Saunders et al. | 435/286 |
| 5,264,184 | 11/1993 | Aysta et al. | 422/101 |
| 5,283,039 | 2/1994 | Aysta | 422/104 |
| 5,552,325 | 9/1996 | Nochumson | 436/177 |
| 5,556,544 | 9/1996 | Didier | 210/436 |
| 5,601,711 | 2/1997 | Sklar et al. | 210/238 |
| 5,603,900 | 2/1997 | Clark et al. | 422/101 |

OTHER PUBLICATIONS

Parasite Detection Efficiencies of Five Stool Concentration Systems, Perry et al. J. Clinical Microbiology Jun., 1990 pp. 1094–1097.

Comparison of the Fekal CON–Trate System with the Formalin–Ethyl Acetate technique for Dectection of Cl. Parasites J. Clin. Micro. Aug. 1985.

Meridan Para–Pak Literature.

Use of a Single Trichrome–Stained Concentrate for the Detection of Intestinal Parasites, Gally Proofs, D. Hale et al.

*Primary Examiner*—Long V. Le
*Attorney, Agent, or Firm*—Parsons Behle & Latimer

[57] ABSTRACT

A multi-filter apparatus for processing ova and parasites from human and animal specimens. The filtration apparatus includes a specimen receptacle, a filter holder section and a collection receptacle. The filter holder section contains two filters, a coarse filter and a fine filter. The method for using the apparatus includes mixing a specimen with a preservation solution to form a mixture, transferring the solution to the specimen receptacle and then fractionating the mixture. After fractionation, the specimen receptacle, filter holder section and supernatant are conveniently discarded. The resulting concentrated parasite sample may be analyzed using conventional analytic techniques. The invention further includes a kit including a filtration apparatus and a preservation fluid dispenser.

34 Claims, 9 Drawing Sheets

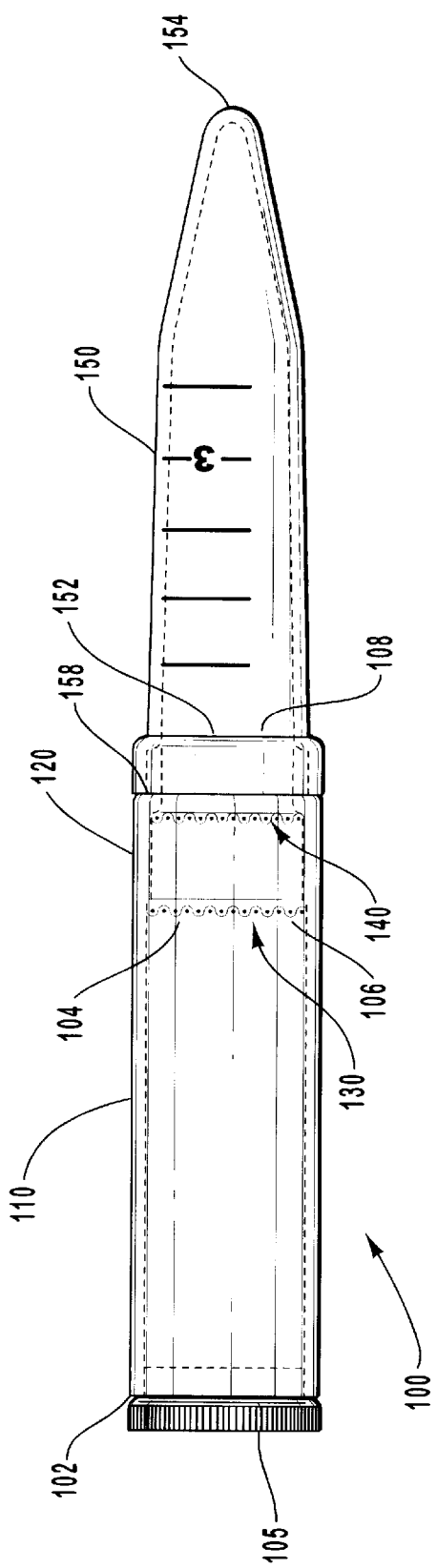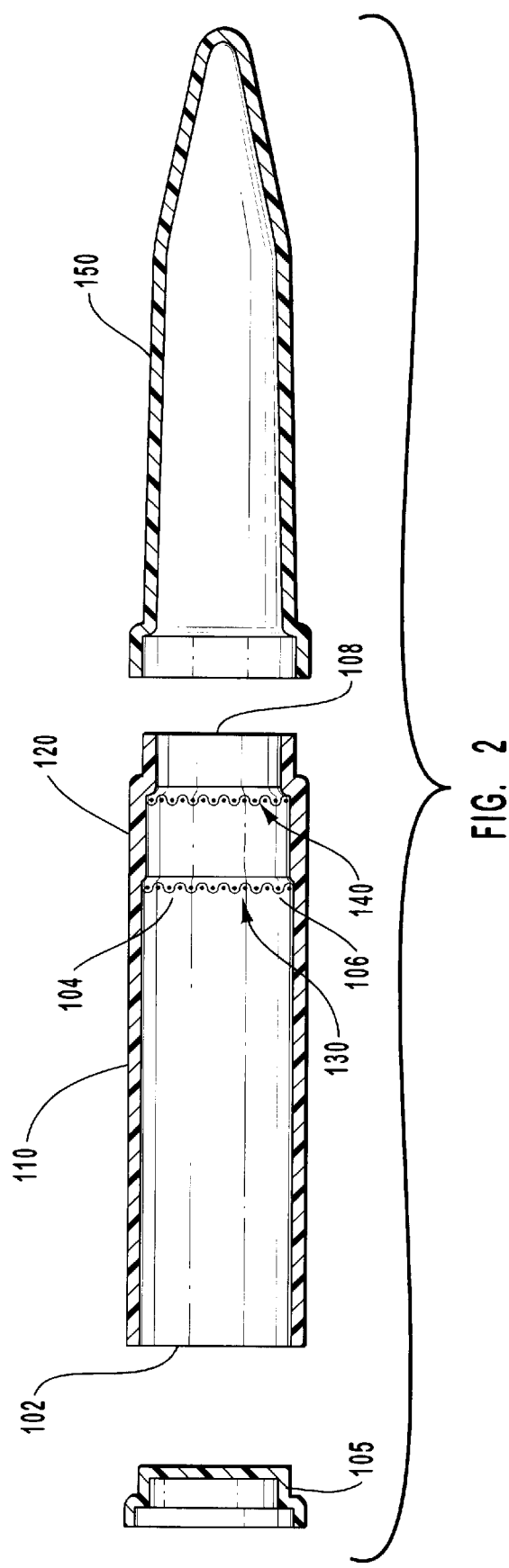

FILTRATION APPARATUS, KIT AND METHOD FOR PROCESSING PARASITE SAMPLES

BACKGROUND OF THE INVENTION

A. Field of the Invention

This invention relates to an apparatus, a kit and method for processing ova and parasites from human and animal specimens. More specifically, this invention relates to a multi-filter apparatus, kit, and method for separating and concentrating ova and parasite from human and animal specimens.

B. Description of Related Art

The prompt diagnosis and treatment of parasitic infections in humans and animals requires simple, fast and accurate diagnostic techniques. Parasitic infections can be diagnosed based on the presence of ova and parasites in human or animal specimens. For example, parasitic infections in the human intestine can be diagnosed by the presence of ova and parasites in a patient's fecal material. Diagnoses based on the presence of ova and parasites are faster because these parasitic forms are more likely to be present in such specimens. The ability to detect ova and parasites is increased when the ova and parasites are separated from residual host material. The separated ova and parasites can then be qualitatively and quantitatively analyzed to determine the nature and extent of the infection.

There is a need for a separation apparatus which quantitatively and non-selectively separates ova and parasites from human or animal specimens while minimizing the amount of residual contaminating material. Such residual material can interfere with subsequent identification and analysis of the collected parasite sample. There is also a need for a separation apparatus which does not require the use of toxic separation chemicals. Prior separation devices typically use toxic chemicals such as ethyl acetate and ether. Finally, prior separation devices typically offer a compromise between efficiency and cost. The present invention overcomes the deficiencies of prior devices by providing a highly efficient, yet inexpensive, multi-filter separation apparatus which minimizes the use of toxic separation chemicals.

One of the traditional methods for collecting ova and parasites is the floatation method. In this method, a specimen, such as fecal material, is dispersed in a flotation solution. The ova and parasites are then collected by adjusting the specific gravity of the solution so that ova and parasites float to the surface, where they are collected on a microscope slide.

A U.S. Patent to R. J. Greenwald (U.S. Pat. No. 4,293,405) describes an apparatus for collecting ova using the floatation method. This patent is incorporated by reference herein in its entirety. In the Greenwald apparatus, a fecal specimen, suspended in a buoyant solution, is placed in a lower tray, and then a single filter is placed over the specimen. Because the filter pore size is greater than 500 micrometers, the filter allows the ova to pass upwards through the filter and collect on the surface of the solution.

A U.S. Patent to T. Addis (U.S. Pat. No. 3,905,895) discloses a similar apparatus and method for separating ova from fecal material. This patent is incorporated by reference herein in its entirety. The Addis apparatus includes a hollow receptacle and a pair of interconnected filtering surfaces. Fecal samples are placed within the receptacle, a flotation solution is added, and the ova are allowed to pass through the filters to the surface of the solution, where they are collected.

A disadvantage of both the Greenwald and Addis devices is that the ova are concentrated at the liquid meniscus, and not in a tight pellet. The large pore size of the filters in the Greenwald and Addis devices also allows contaminating matter to collect at the liquid surface with the ova. This residual material interferes with analysis of the parasite samples.

Another method for separating ova and parasites from fecal material is filtration prior to a gravimetric centrifugation separation. In this method, the sample is first filtered through a filter to remove large contaminants. Then, diethyl ether is added to "defat" the specimen solution. After separation by centrifugation, 4 layers were formed: an ether layer, a debris layer, a formalin layer and a pellet containing ova and parasites. After decanting the first three layers, the pellet was analyzed for the presence of ova and parasites. A later improvement in this method substituted ethyl acetate for diethyl ether to reduce the risk of fire or explosion.

A U.S. Patent to W. S. Zierdt (U.S. Pat. No. 4,081,356) discloses an apparatus and method for collecting ova and parasites using the traditional formalin ether method. This patent is incorporated by reference herein in its entirety. The Zierdt apparatus includes a single filter juxtaposed between emulsification and separation chambers. Emulsified fecal samples are transferred from the emulsification chamber to the separation chamber by vertical agitation. After transfer of the sample to the emulsification chamber, the ova and parasites are subsequently concentrated using the formalin-ether method.

A disadvantage of the Zierdt apparatus is that the pore size of the single filter must be sufficiently large to allow transfer of the parasite sample through the filter using vertical agitation. Typically, only large residual material is trapped by the filter. Vertical agitation can also generate fine sediment which contaminates the parasite sample. The Zierdt apparatus is also designed for use of hazardous chemicals such as diethyl ether, which create a fire and explosion hazard.

A U.S. Patent to M.-G. Chang (U.S. Pat. No. 5,066,463) discloses a multi-purpose fecal examination apparatus for performing occult blood tests as well as inspecting fecal samples for parasites. This patent is incorporated by reference in its entirety. Fecal samples are inserted into a hollow tube within the apparatus. Filter paper impregnated with test reagent may be placed in contact with the sample within two windows in the apparatus. After testing is complete, the fecal samples are drained through a single filter into a collection device such as a test tube. Because the examination apparatus lacks a self-contained collection tube, the use of this apparatus increases the likelihood that fecal samples will be lost or will contaminate the user. Because the filtration apparatus includes only a single filter, and is designed to collect the sample by draining the sample through a filter, the apparatus requires a large pore size and allows residual material to collect with the parasite sample.

Perry et al. reviewed the effectiveness of five different filtration devices, including the Zierdt apparatus described above (Perry, J. L., Matthews, J. S., and Miller, G. R. "Parasite Detection Efficiencies for Five Stool Concentration Systems." Journal of Clinical Microbiology, vol. 28, no.2 (June 1990), pp. 1094–1097). This article is incorporated by reference in its entirety. These filtration devices were used for the removal of large debris before a traditional centrifugation concentration procedure, such as the formalin-ether or formalin-ethyl-acetate methods. The devices have large filter pore sizes ranging from 600 to 2,000 micrometers. While all tested devices detected all six test organisms, the efficiencies of detection were generally low.

Other methods of analyzing specimens for the presence of parasites utilize non-filtration techniques. For example, U.S. Patents to H. Adlercreutz et al. (U.S. Pat. No. 4,427,769) and M. A. Grow and V. D. Shah (U.S. Pat. No. 5,094,956) disclose methods for testing fecal samples for hemoglobin by immunoassay testing. These patents are incorporated by reference herein in their entirety. Such tests are not designed to facilitate visual detection or identification of ova and parasites from fecal samples.

The present invention overcomes the deficiencies of prior devices by providing a multi-filter apparatus for quantitatively separating ova and parasites from human and animal specimens and for concentrating the parasite samples. The multi-filter apparatus eliminates the need for separate filtration and separation steps by performing both steps at the same time. An additional advantage is that the use of toxic chemicals such as diethyl ether and ethyl acetate is eliminated. The multi-filter apparatus may be used a part of a specimen-processing kit.

The present invention also includes a method for processing human and animal specimens by mixing the specimen in a preservation solution, transferring the specimen-containing solution to a specimen receptacle and then fractionating the mixture in the multi-filter apparatus. During fractionation, the ova and parasites are concentrated in a collection receptacle. The concentrated ova and parasites are then conveniently separated from the supernatant and are ready for subsequent analysis.

II. SUMMARY OF THE INVENTION

It is an object of the invention to provide a filtration apparatus which efficiently separates ova and parasites from a human or animal specimen. It is a feature of the invention that the filtration apparatus incorporates multiple filters to retain residual contaminating material while selectively allowing ova and parasites to pass through the filters. It is an advantage of the invention that the pore size of the first filter may be greater than that of the second filter so that coarse material is trapped on the first filter while finer material is trapped on the second filter. This filter design prevents clogging of the filters and prevents ova and parasites from becoming trapped in contaminating residual material. It is a further advantage of the invention that the concentrated ova and parasites are substantially free of residual material from the specimen.

It is an object of the invention to provide a filtration apparatus which facilitates fast separation of ova and parasites from human and animal specimens. It is a feature of the invention that the filtration apparatus efficiently separates ova and parasites by centrifugation. It is an advantage of the invention that the filtration apparatus is cost-effective.

It is an object of the invention to provide a separated parasite sample which is substantially free of contaminating material. It is an feature of the invention that the absence of residual contaminating material improve the quality and accuracy of subsequent analysis. It is an advantage of the invention that the separated parasite sample can be analyzed using a variety of analytical techniques including visual examination, chemical staining and immunological assay.

It is an object of the invention to provide a filtration apparatus which is inexpensive and simple to use. It is a feature of the invention that the filtration apparatus can be made from a variety of materials, including plastics. It is an advantage of the invention that the filtration apparatus may be transparent or translucent, allowing visual inspection of the specimen-containing solution before and after separation.

It is an object of the invention to provide a leak-proof apparatus which is safe to use. It is a feature of the invention that the filtration apparatus prevents contamination of the user and testing equipment. It is an advantage of the invention that the filtration apparatus is inexpensive, so that the contaminated apparatus can be readily discarded after use. It is an additional advantage of the invention that the apparatus eliminates the use of dangerous separation chemicals such as ether and ethyl acetate.

These and other objects, features and advantages of the invention will be clear to a person of ordinary skill in the art upon reading this specification in light of the appending drawings.

III. BRIEF DESCRIPTION OF THE DRAWINGS

FIG. 1 depicts an assembled view of the preferred embodiment of the filtration apparatus.

FIG. 2 depicts a partially disassembled view of the preferred embodiment of the filtration apparatus.

IV. DETAILED DESCRIPTION OF THE PREFERRED EMBODIMENTS

Figures 3, 4:
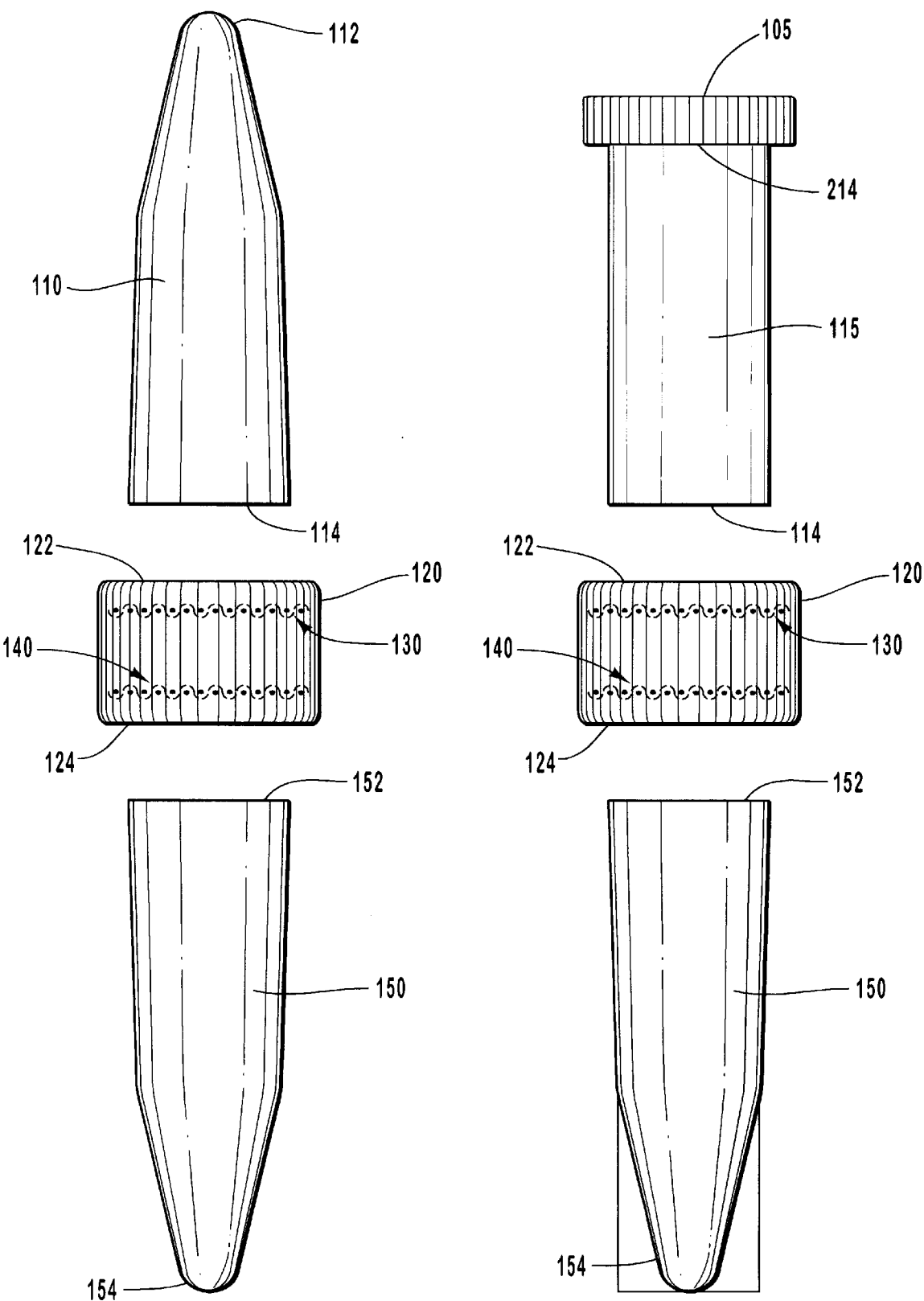
FIG. 3 depicts a disassembled view of another embodiment of the filtration apparatus.
FIG. 4 depicts a view of an alternate embodiment of the filtration apparatus.

The present invention of a multi-filter separation apparatus facilitates the collection and analysis of ova and parasites from human and animal specimens. The specimens which may be analyzed include, but are not limited to, fecal material, duodenal aspirates, gastric aspirates and sputum. In a preferred embodiment of the invention, such specimens are preferably fecal material.

A. The Multi-filter Separation Apparatus

Referring to FIGS. 1 and 2, in the preferred embodiment of the invention, multi-filter apparatus 100 has a unibody design with a removable cap. Apparatus 100 includes specimen receptacle 110, filter holder section 120 and collection receptacle 150. Specimen receptacle 110 has an open end 102 and a filter holder section-joining end 104. Cap 105 engages open end 102 of specimen receptacle 110. Cap 105 may either insert into open end 102 or cover the outside of open end 102. Cap 105 preferably sealingly engages open end 102 prevent leakage of the specimen/preservation solution mixture. Cap 105 may include a sealing engagement mechanism such as a protruding lip on cap 105 or at end 102 or both. The sealing engagement mechanism may further include a channel on cap 105 or at end 102 for receiving the protruding lip. The sealing mechanism may also include a screw and thread mechanism, a tight friction fit or a gasket or similar sealing mechanism, as will be appreciated by those of ordinary skill in the art.

Filter holder section 120 has a specimen receptacle-joining end 106 and collection receptacle-joining end 108. Filter holder section 120 is in fluid communication with specimen receptacle 110. As shown in FIGS. 1 and 2, in the best mode of the invention filter holder section 120 is integral with specimen receptacle 110. Filter holder section 120 includes coarse filter 130 and fine filter 140. Coarse filter 130 is located proximal to specimen receptacle 110 while fine filter 140 is located proximal to collection receptacle 150.

In a preferred embodiment of the invention, filters 130 and 140 are spaced apart. The spacing between filters 130 and 140 may be adjusted according to the specimen volume and amount of residual material which may collect between the coarse and fine filters. In a more preferred embodiment of the invention, the spacing between the filters may range from about 0.5 cm to about 2 cm, although greater and less spacings may be used in some embodiments. In a less preferred embodiment of the invention, coarse filter 130 may be placed in contact with fine filter 140.

Coarse filter 130 and fine filter 140 allow fluid communication between specimen receptacle 110 and collection receptacle 150. In the preferred embodiment of the invention, the average pore size of coarse filter 130 is greater than or equal to the pore size of fine filter 140. In the most preferred embodiment of the invention, the pore size of coarse filter 130 is greater than the pore size of fine filter 140. The pore sizes of filters 130 and 140 may range from about 180 to about 295 micrometers. In a preferred embodiment of the invention, the pore size of coarse filter 130 ranges from about 215 to about 295 micrometers, and the pore size of fine filter 140 ranges from about 180 to about 250 micrometers. In the best mode of the invention contemplated by the inventor, coarse filter 130 has a pore size of about 250 micrometers and fine filter 140 has a pore size of about 215 micrometers.

Referring to FIG. 5, coarse filter 130 and fine filter 140 may be attached to filter holder section 120 by any suitable attachment mechanism. The same or different attachment mechanism may be used for each filter. Referring to FIG. 5A, either filter may be attached by securing the filter against a ledge 126. The filter may be held in place by a friction fit, by a gasket or other securing ring or by a glue or other bonding mechanism, or by any other suitable mechanism, as will be appreciated by those of ordinary skill in the art. Either filter may also be attached within filter holder section 120 by securing it against a porous end wall 127. Porous end wall 127 has one or more apertures which allow filtered specimen solution to pass into collection receptacle 150. The filters may be held in place by a friction fit, by a gasket, a securing ring, by a glue or other bonding mechanism, or any other suitable mechanism.

Figure 5A:
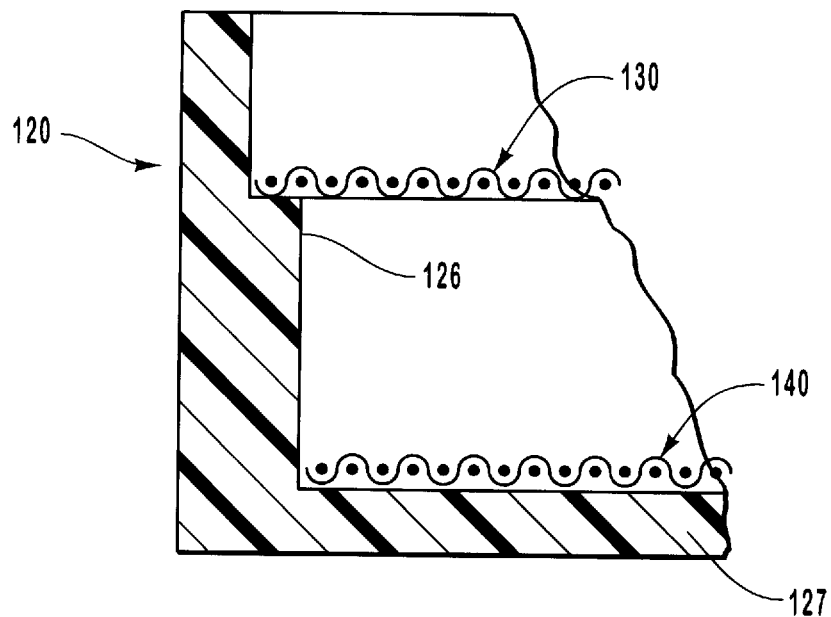
FIG. 5A depicts a partial cross-sectional view of a filter attachment mechanism securing a filter against a ledge.
Figure 5B:
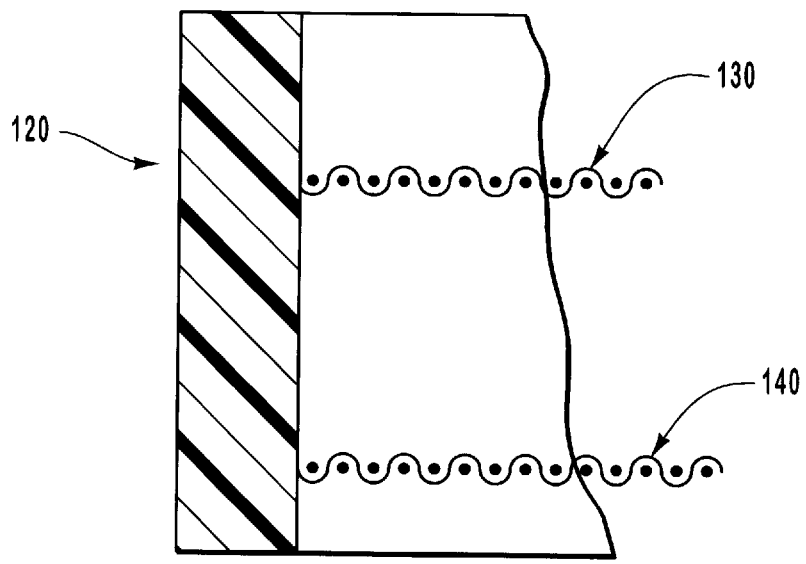
FIG. 5B depicts a partial cross-sectional view of a filter attachment mechanism in which the filters are integrally attached to the filter holder section.
Figure 5C:
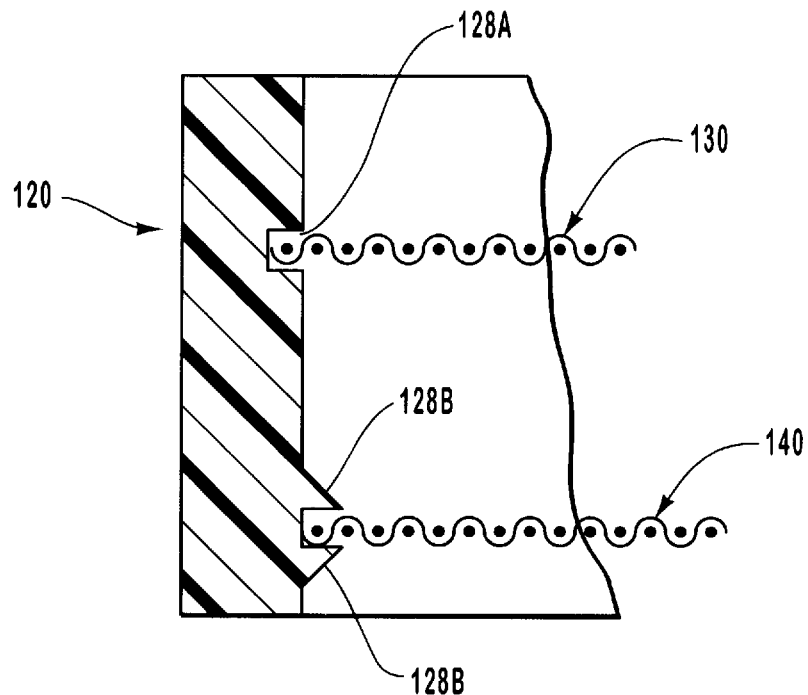
FIG. 5C depicts a partial cross-sectional view in which the filters are secured in the filter holder section by insertion into a slot, or between internal projections.
Figure 5D:
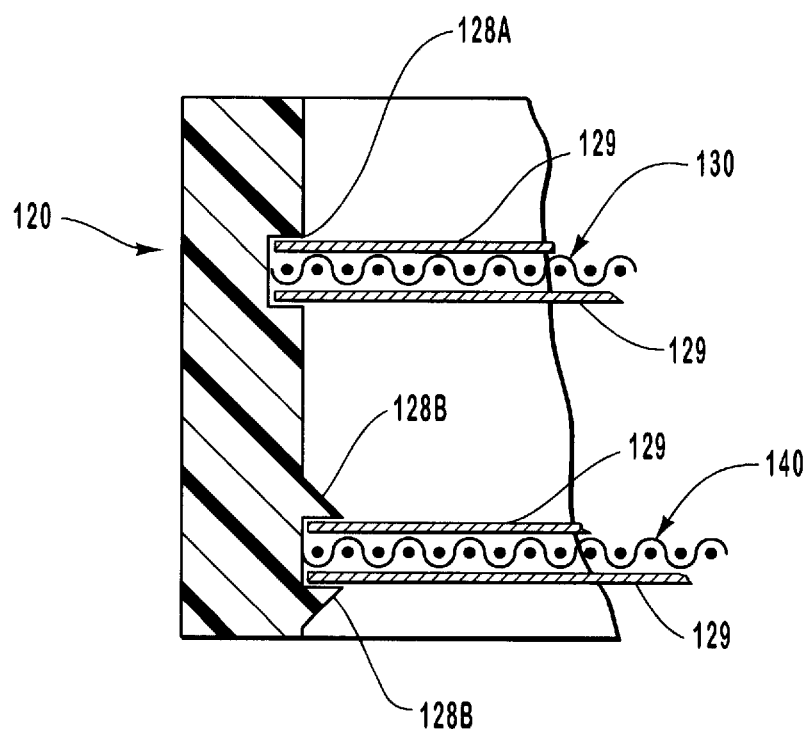
FIG. 5D depicts a partial cross-sectional view in which the filters are secured in the filter holder section with a casket or retaining ring in combination with a slot or internal projections.

Referring a FIG. 5B, either filter may be integrally attached to filter holder section 120 by forming the filter and holder as a single unit. Alternatively, a filter may be attached to filter holder section 120 by glue or other bonding mechanism. Referring to FIG. 5C, either filter may be attached to filter holder section 120 by inserting the filter into a slot 128A or between internal projections 128B. Referring to FIG. 5D, a filter may also be attached to filter holder section 120 using gasket or retaining ring 129 in combination with groove 128A or projections 128B. Either filter may also be attached using a combination of any of the attachment mechanisms described above.

Figure 5E:
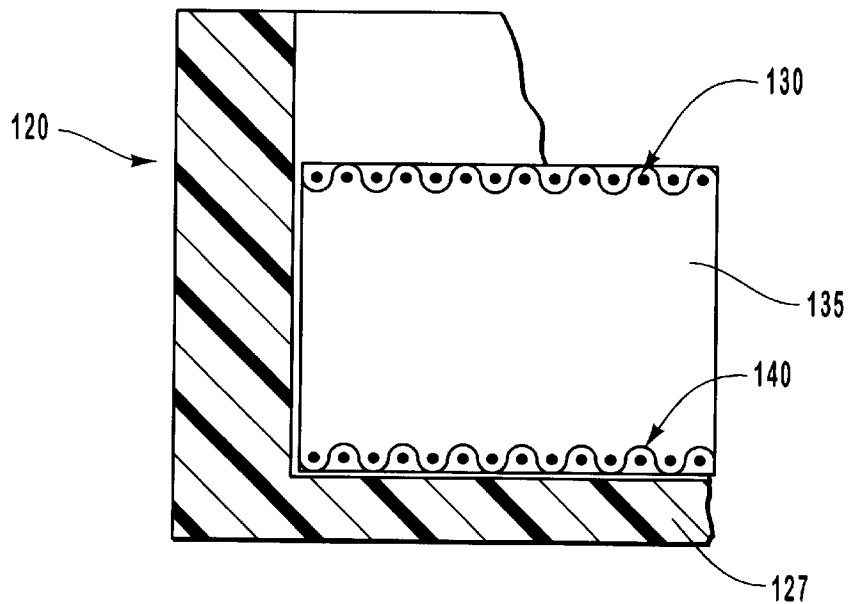
FIG. 5E depicts a partial cross-sectional view in which the filters are part of a filter cartridge within the filter holder section.

Referring to FIG. 5E, filters 130 and 140 may also be part of a filter cartridge insert 135. Insert 135 fits inside specimen receptacle 110 within filter holder section 120. Insert 135 may be supported by a ledge 126 or porous end wall 127 during centrifugation. In the preferred embodiment, filter cartridge 135 sealingly engages specimen receptacle 110 or filter holder section 120 to prevent specimen fluid from bypassing the filters.

Referring to FIG. 7, coarse filter 130 and fine filter 140 may be self-supporting within filter holder section 120. In another embodiment of the invention, either or both filters may be supported by a support screen 565. Suitable arrangements of filters and support screens include those shown in FIGS. 7A and 7B. Support screen 565 may be combined with any suitable attachment mechanism. Referring to FIG. 7C, support screen 565 may have any suitable grid pattern, including a grid or cross-hair pattern.

Referring to FIGS. 1 and 2, collection receptacle 150 receives the filtered specimen/preservation solution mixture. Collection receptacle 150 has a filter holder section-joining end 152 and a closed end 154. Collection receptacle 150 is in fluid communication with specimen receptacle 110 through filter holder section 120. In one preferred embodiment of the invention, collection receptacle 150 is a separate piece and is not integral with filter holder section 120. In a more preferred embodiment of the invention, filter holder section-joining end 152 is integral with collection receptacle-joining end 108 of filter holder section 120.

In the best mode of the invention, collection receptacle 150 is integral with specimen receptacle 110—filter holder section 120, but may be separated from section 120 at a pre-determined separation area. Such a separation area may be a weakened area line 158 which is created by a score line on body of filtration apparatus 100. Alternatively, the separation area may have a thinner layer of outer body material. The scope of the invention is intended to include other suitable separation mechanisms known to those of ordinary skill in the art.

After separation of collection receptacle 150 from apparatus 100, receptacle 150 may be capped. In the best mode of the invention contemplated by the inventor, end 152 of collection receptacle 150 is closed with cap 105 in the same manner as for end 102 of specimen receptacle 110. A sealing engagement may be formed by any suitable sealing mechanism, including those described above.

Closed end 154 of collection receptacle 150 may have any desired shape, including conical, rounded, square or frusto-conical. In a preferred embodiment of the invention, closed end 154 is conical or frusto-conical to facilitate collection of the ova and parasites in the tip. In the most preferred embodiment of the invention, closed end 154 is integral with collection receptacle 150 to prevent loss or leakage of the specimen or preservation solution.

Referring to FIG. 3, in a second preferred embodiment of the invention, multi-filter apparatus 100 includes specimen receptacle 110, a separable filter holder section 120 and collection receptacle 150. Specimen receptacle 110 has a closed end 112 and a filter holder section-receiving end 114. Closed end 112 may have any desired shape, including conical, rounded, square or frusto-conical. Closed end 112 of specimen receptacle 110 is preferably integral with specimen receptacle 110 to prevent leakage of the specimen solution.

Separable filter holder section 120 has a specimen receptacle-joining end 122 and collection receptacle-joining end 124. When filter holder section-joining end 114 engages specimen receptacle-joining end 122, specimen receptacle 110 is in fluid communication with filter holder section 120. End 114 may receive or be inserted into end 122.

Filter holder section-receiving end 114 preferably sealingly engages specimen receptacle-joining end 122 to prevent leakage of the specimen/preservation solution mixture. The sealing engagement between end 114 and end 122 may be formed by any suitable sealing mechanism, as will be appreciated by those in the art. Such a sealing mechanism may include a protruding lip on either end 114 or 122; the other end may include a lip or groove which grippingly and sealingly engages the protruding lip. The sealing mechanism may also include a screw and thread mechanism or a tight friction fit between ends 114 and 122. The sealing mechanism may further include a gasket or similar sealing component. In a more preferred embodiment of the invention, end 114 is inserted into end 122 and sealed by a friction fit.

Filter holder section 120 includes coarse filter 130 and fine filter 140, as described above. Referring to FIGS. 5A through 5E, coarse filter 130 and fine filter 140 may be attached to filter holder section 120 by any suitable attachment mechanism, or combination of attachment mechanisms, as described above. The same or different attachment mechanisms may be used for each filter. Referring to FIG. 7, either filter may be supported by a support screen 565, as described above.

Figure 6:
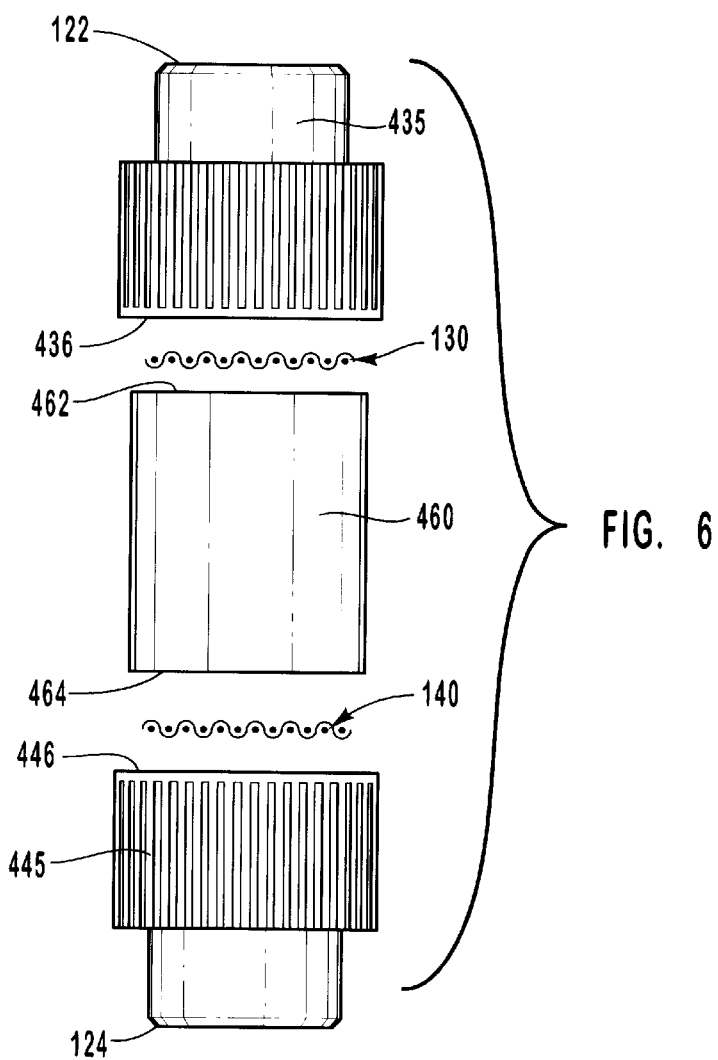
FIG. 6 depicts another embodiment of the filter holder section.
Figure 7A:
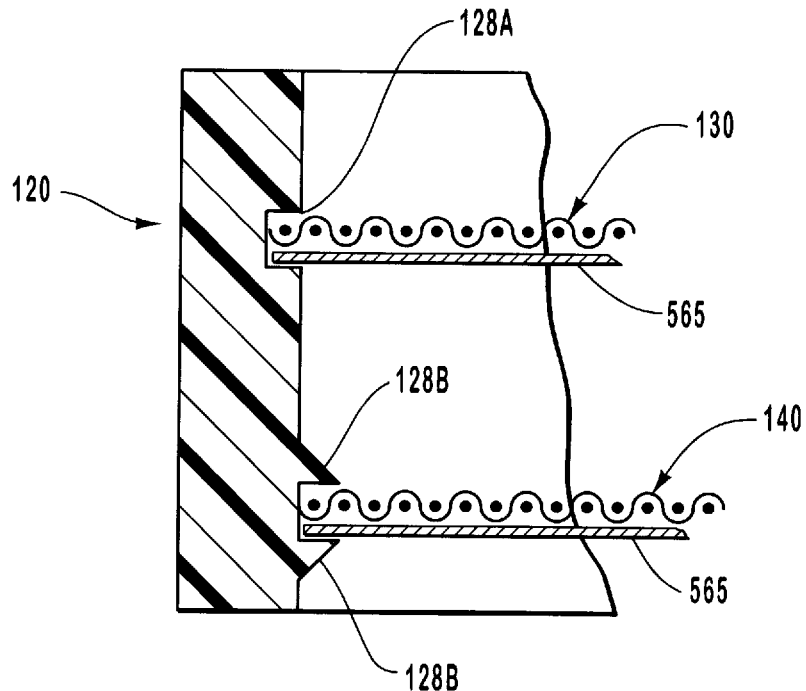
FIG. 7A depicts a partial cross section showing one embodiment of the filter holder section using a support screen and a filter attachment mechanism.
Figure 7B:
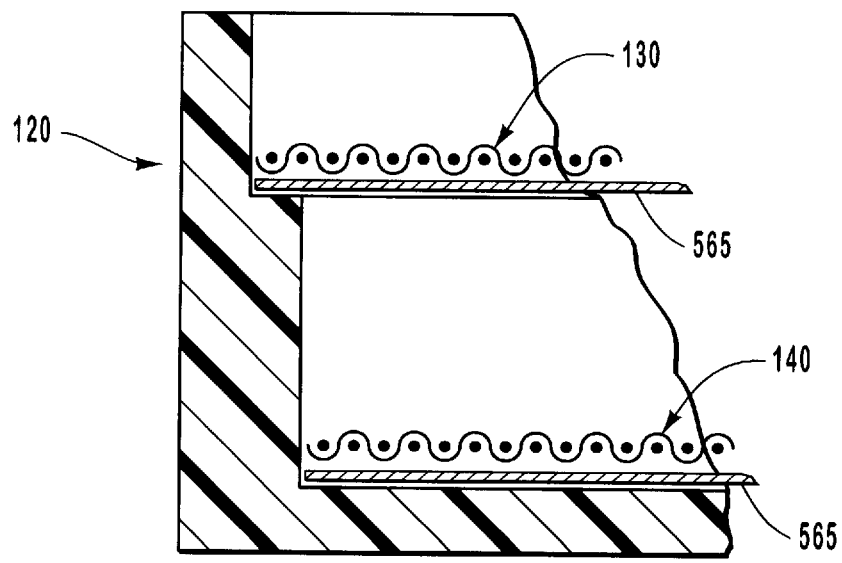
FIG. 7B depicts a partial cross section showing additional embodiments of the filter holder section using a support screen with other attachment mechanisms.
Figure 7C:
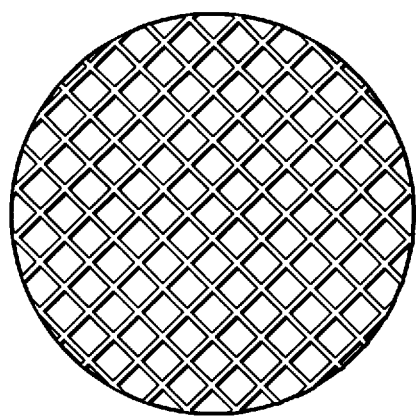
FIG. 7C depicts an embodiment of the grid pattern of the support screen.
Figure 7D:
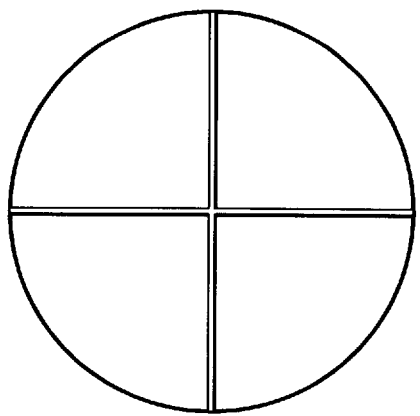
FIG. 7D depicts another embodiment of the grid pattern of the support screen.

Referring to FIG. 6, another embodiment of the filter holder section includes a first section end 435, a section second end 445 and a connecting tube 460. A coarse filter holding mechanism is formed by the sealing engagement of open end 436 of first section end 435 with end 462 of connecting tube 460. A fine filter holding mechanism is formed by the sealing engagement of open end 446 of second section end 445 with end 464 of connecting tube 460. Any suitable attachment mechanism, support screen and sealing engagement mechanism may be used in this embodiment of the filter holder section.

Referring to FIG. 3, collection receptacle 150 receives the filtered specimen/preservation solution mixture. As described above, collection receptacle 150 has a filter holder section-joining end 152 and a closed end 154. When filter holder section-joining end 152 engages specimen receptacle-joining end 124, collection receptacle 150 is in fluid communication with filter holder section 120. End 152 may receive or be inserted into end 124. In a preferred embodiment of the invention, filter holder section-joining end 152 of collection receptacle 150 sealingly engages collection receptacle joining end 124 of filter holder section 120. This sealing engagement may be formed by any suitable sealing mechanism, including those described above.

Closed end 154 of collection receptacle 150 may have any desired shape, including conical, rounded, square or frusto-conical. In a preferred embodiment of the invention, closed end 154 is conical or frusto-conical to facilitate collection of the ova and parasites in the tip. In the most preferred embodiment of the invention, closed end 154 is integral with collection receptacle 150 to prevent loss of the parasite specimen or preservation solution.

Referring to FIG. 4, in an alternate embodiment specimen receptacle 110 may be a separate cap 105 and reservoir 115. Cap 105 is removable for addition of sample into reservoir 115 through aperture 214. Cap 105 may insert into or cover aperture 214. Cap 105 preferably sealingly engages aperture 214 of reservoir 115 by any suitable sealing mechanism, including those described above. In a more preferred embodiment of the invention, cap 105 can also close end 152 of collection receptacle 150.

Specimen receptacle 110, collection receptacle 150 and filter holder section 120 may be independently manufactured from any suitable material. In a preferred embodiment of the invention, receptacles 110 and 150 and tube holder section 120 are made from a plastic material. Such plastic materials may include, but are not limited to, polyethylene, polypropylene, polystyrene, and mixtures of these plastic materials. In alternate embodiments of filtration apparatus 100, glass or metal may be used to manufacture part or all of the apparatus. Receptacles 110 and 150 are also preferably transparent or translucent to allow visual inspection of the contents. In the best mode of the multi-filter apparatus contemplated by the inventor, the specimen and collection receptacles are made of semi-transparent polypropylene.

Filters 130 and 140 may be made of any suitable filter material. Filters 130 and 140 may be different materials. Such material may include, but is not limited to, nylon, teflon, polypropylene, nitrocellulose, metals such as copper, nickel and stainless steel, and other suitable synthetic plastics materials. In a more preferred embodiment of the invention, the filters are resistant to chemicals present in the preservation solution. Such chemicals may include formalin and alcohol. In the best mode of the invention contemplated by the inventor, filters 130 and 140 are stainless steel.

In some preferred embodiments of the invention, filters 130 and 140 may be reinforced with suitable reinforcing materials so that the filter is resistant to collapse during centrifugation. Such reinforcing materials may include, but are not limited to, a metal, plastic or fiber reinforcement. If a support screen is used, the support screen 125 may be made from any suitable material, including but not limited to, metal, plastic and fiber.

The fluid capacity of collection receptacle 150 is preferably about the same as capacity of specimen receptacle 110. The fluid capacities of the specimen and collection receptacles are determined according to the type and amount of specimen being fractionated, as will be appreciated by those of ordinary skill in the art. In a more preferred embodiment of the invention, the fluid capacities of the specimen and collection receptacles will range from about 1 to about 10 milliliters, although greater or lesser capacities are within the scope of the invention. In the best mode, the fluid capacities of the specimen and collection receptacles are about 7 milliliters.

B. Methods of Using the Filtration Apparatus

Figure 9:
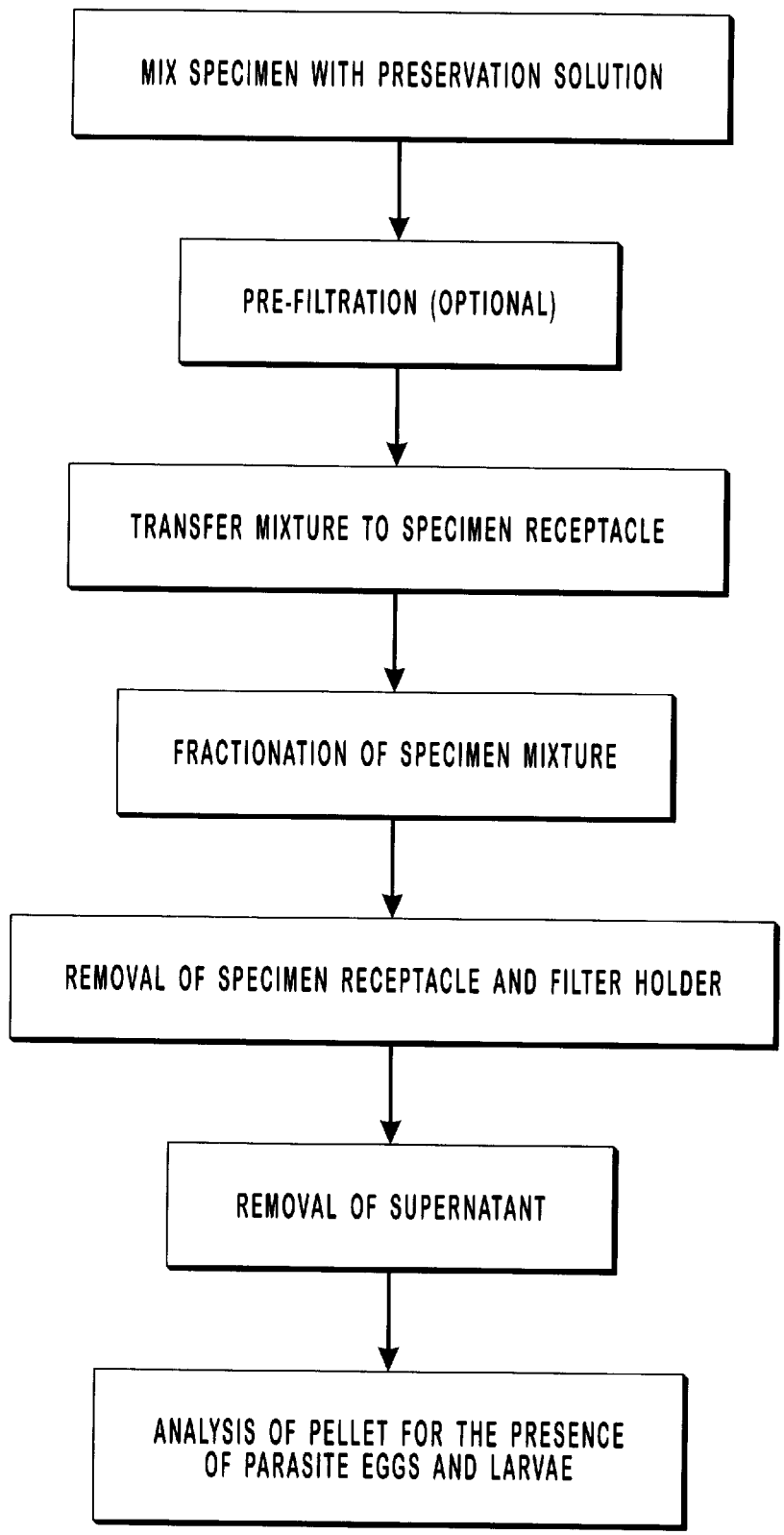
FIG. 9 depicts a preferred method of using the filtration apparatus to analyze human or animal specimens.

Referring to FIG. 9, the preferred method of using the filtration apparatus is illustrated. First, a human or animal specimen is suspended in a suitable preservation solution to form a specimen/preservation solution mixture. Suitable preservation solutions may include, but are not limited to, 5–10% buffered neutral formalin, 37% aqueous neutral formalin, ECO-SAFE (Meridian Diagnostics), PARA-SAFE (Scientific Device Labs), polyvinylalcohol solution with cupric sulfate, zinc or mercury, sodium acetic formaldehyde, methiolate-iodine-formaldehyde, CON-SED, PROTO-FIX (Alpha-Tec), and other preservation solutions known to those of ordinary skill in the art. In a more preferred embodiment of the invention, the preservation solution will include fixative, buffering or anti-gelling agents. In the best mode, the preservative solution is a formalin-containing solution or a formalin-substitute.

In the best mode of the invention, the specimen solution is not washed before fractionation. In an alternate embodiment of the invention, the specimen may be washed prior to fractionation. The specimen/preservation solution mixture is centrifuged for about 2–15 minutes at about 2,000 rpm in a clinical centrifuge. After centrifugation, the supernatant is discarded and the pellet is suspended in 0.085% saline to form a washed specimen solution. The volume of the washed specimen solution is preferably about 5–7 milliliters. The washed specimen solution is then treated the same as the specimen/preservation solution mixture in the following steps.

Figure 10A:
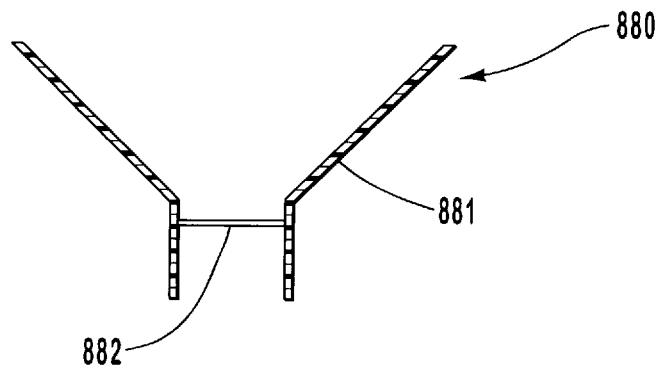
FIG. 10A depicts a cross-section of one embodiment of a pre-filter, a funnel with a screen.

The specimen/preservation solution mixture may optionally be pre-filtered to remove large particulate material which inhibits separation of the ova and parasites from the residual contaminating material. Such pre-filtration may include passing the mixture through one or more layers of a flexible screening material such as cheesecloth, stainless steel, gauze, copper or plastic filters. Referring to FIG. 10A, the specimen/preservation solution mixture may also be pre-filtered using a device such as pre-filter 880 which includes funnel 881 containing macro-filter 882. Macro-filter 882 may be stainless steel, gauze, copper or plastic. The pore size of the macro-filter can range from about 500 to about 5000 micrometers, or larger. Alternatively, an apparatus such as that described by Zierdt (U.S. Pat. No. 4,081,356) can be used to pre-filter the mixture.

Figure 10B:
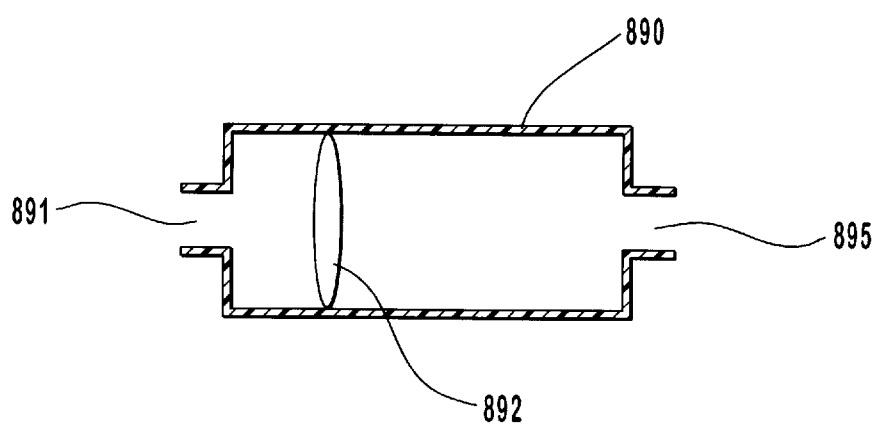
FIG. 10B depicts a cross-section of another embodiment of a pre-filter, a cartridge containing a screen.

After forming the specimen/preservation solution mixture, and any optional pre-filtration step, the mixture is transferred to specimen receptacle 110. The mixture may be poured into end 102, 114 or 214 of a suitable specimen receptacle. Alternatively, if a pre-filtration apparatus is used, the pre-filtration apparatus may be connected to the end such that the pre-filter mixture flows directly into specimen receptacle 110. Referring to FIG. 10b, transfer of the mixture to specimen receptacle 110 can also include the use of a pre-filtration cartridge 890 with macro-filter 892. The solution enters end 895, flows through pre-filter 892 and then exits end 891 into specimen receptacle 110. In a more preferred embodiment of the invention, end 891 of cartridge 890 sealingly engages 102, 114 or 214 of specimen receptacle 110. Although not generally necessary, after transfer of the mixture to specimen receptacle 110, the volume of the mixture may be adjusted to achieve the optimal desired specimen dilution. Suitable diluents include preservation solution and 0.085% saline.

In the best mode of the invention contemplated by the inventor, multi-filter apparatus 100 is used in combination with a preservation solution dispenser. Such a dispenser may use any suitable preservation solution for stabilizing ova and parasites, including the preservation solutions described above. Although one type of dispenser is illustrated below, multi-filter apparatus 100 may be used with any suitable dispenser, as will be appreciated by those of ordinary skill in the art.

Figure 8:
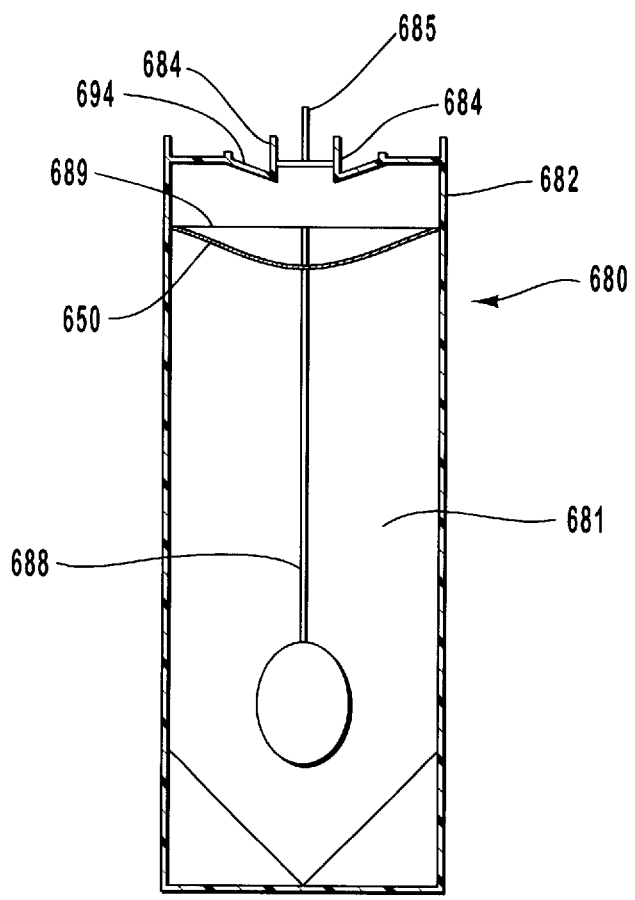
FIG. 8 depicts a view of an example of a preservation fluid dispenser.

Referring to FIG. 8, an example of such a preservation solution dispenser 680 is the PARA-PAK Ultra dispenser (Meridian Diagnostics, Inc., Cincinnati, Ohio). Dispenser 680 contains 10% buffered neutral formalin as a preservation solution. A human or animal specimen may be placed into dispenser 680 using a specimen transferring device such as such as spatula 688. After mixing of the specimen with the preservation solution to form a specimen/preservation solution mixture, the mixture may be transferred from the dispenser to specimen receptacle 110. In the best mode, a portion of cap 682 is adapted to sealingly engage end 102, 114 or 214 of specimen receptacle 110 so that the mixture can be directly transferred without contaminating the user.

In one embodiment of the invention, end 689 of dispenser 680 directly engages end 102, 114 or 214 of specimen receptacle 110. Such an engagement mechanism may include, but is not limited to, a protruding lip on either end; the other end may include a lip or groove which grippingly and sealingly engages the protruding lip. The engagement mechanism may also include a screw and thread mechanism or a tight friction fit between the ends. The sealing mechanism may further include a gasket or similar sealing component.

In another preferred embodiment of the invention, dispenser 680 includes a cap 682 with a tab and removable portion 685. Adjacent to tab and removable portion 685 is sleeve 684, which is adapted to sealingly engage an end of the specimen receptacle. After disconnecting tab and removable portion 685, end 102, 114 or 214 of specimen receptacle 110 is connected to sleeve 684, and then the mixture is transferred to specimen receptacle 110. Sleeve 684 may receive or insert into the end of specimen receptacle 110.

In the most preferred embodiment, cap 682 includes engagement ring 694. The end of the specimen receptacle 110 can be inserted into engagement ring 694 and form a sealing engagement for transfer of the specimen/preservation solution mixture after removal of tab and removable portion 685.

The preservation solution dispenser may further includes a pre-filter 650. The preferred pore size of pre-filter 650 ranges from about 500 to 5,000 micrometers. Pre-filter 650 may form part of cap 682 of dispenser 680. Transfer of the specimen/preservation solution mixture can be effected by gravity, by applying pressure to the dispenser, by centrifugation, or by any other suitable method, as will be appreciated by those of ordinary skill in the art.

After transfer of the specimen/preservation solution mixture to specimen receptacle 110, the mixture is then centrifuged to fractionate the mixture. In the preferred embodiment of the invention, centrifugation occurs for about 2–15 minutes at 2000 rpm in a clinical centrifuge. After centrifugation, collection receptacle 150 is disconnected from filter holder section 120. The supernatant is discarded, and the pellet in collection receptacle 150 is analyzed for the presence of ova and parasites. To prevent leakage or spillage of the sample, collection receptacle 150 may be closed with cap 105.

C. Methods of Detecting Ova and Parasites

The fractionated specimen may be analyzed according to standard analytic techniques. Such methods of analysis include an iodine wet mount, trichrome staining and a modified trichrome staining procedure. In the best mode of the invention contemplated by the inventor, specimens stained using a modified trichrome staining procedure.

D. Experimental Data

The following experiments compare the efficiencies of recovery of different types of parasite samples, either singly or in combination, using the instant invention of a multi-filter apparatus, as compared with a conventional analytic method, formalin/Hemo-De concentrated specimens (designated "O & P"). In each study, except for the column labeled O & P, the first and second paired numbers correspond to the average pore size of the coarse and fine filters, respectively, used in the multi-filter apparatus.

In each study, a sample volume of 5 milliliters was analyzed using either the O & P method or the multi-filter apparatus. The number of ova or parasites detected per 50 $\lambda$ aliquot of concentrated sediment is shown in the first row. The number of organisms per 50 $\lambda$ aliquot lost is shown in row 2. For the O & P method, the number of organisms lost is the number in the wash and in the debris plug. For the multi-filter apparatus, the number of organisms lost is the number trapped on each filter. The amount of debris on each filter is shown in the third row, where 1+, 2+, 3+ and 4+ indicate that the respective filter was about 25%, 50%, 75% or 100% covered with debris.

---

SPECIMEN 1:
Organism: *Diphyllobothrium latum*
Original sample: 1 *Diphyllobothrium latum* egg per 50 $\lambda$ aliquot Concentration Sediment:
(organisms per 50 $\lambda$ aliquot)

| ORGANISM | O&P | 295/295 | 295/250 | 295/215 | 250/250 | 250/215 | 215/215 |
|---|---|---|---|---|---|---|---|
| *D. latum* | 5 | 5 | 14 | 13 | 14 | 8 | 14 |

Organisms Lost:
(organisms per 50 $\lambda$ aliquot)

| ORGANISM | O&P wash/debris plug | 295/295 | 295/250 | 295/215 | 250/250 | 250/215 | 215/215 |
|---|---|---|---|---|---|---|---|
| *D. latum* | 0/0 | 0/0 | 0/0 | 0/0 | 0/0 | 0/0 | 0/0 |

Amount of debris on filters:

| FILTER SIZE Top/Bottom | | 295/295 | 295/250 | 295/215 | 250/250 | 250/215 | 215/215 |
|---|---|---|---|---|---|---|---|
| DEBRIS | | 0/1+ | 0/1+ | 0/1+ | 1+/1+ | 2+/1+ | 3+/2+ |

1+ = 25% of filter covered with debris
2+ = 50% of filter covered with debris
3+ = 75% of filter covered with debris
4+ = 100% of filter covered with debris

---

SPECIMEN 2:
Organism: *Ascaris lumbricoides*
Original sample: 1 *Ascaris lumbricoides* egg per 50 $\lambda$ aliquot Concentration Sediment:
(organisms per 50 $\lambda$ aliquot)

| ORGANISM | O&P | 295/295 | 295/250 | 295/215 | 250/250 | 250/215 | 215/215 |
|---|---|---|---|---|---|---|---|
| *A. lumbricoides* | 18 | 51 | 53 | 58 | 71 | 65 | 80 |

Organisms Lost:
(organisms per 50 $\lambda$ aliquot)

| ORGANISM | O&P wash/debris plug | 295/295 | 295/250 | 295/215 | 250/250 | 250/215 | 215/215 |
|---|---|---|---|---|---|---|---|
| *A. lumbricoides* | 0/0 | 0/0 | 0/0 | 0/0 | 0/0 | 1/1 | 6/1 |

Amount of debris on filters:

FILTER SIZE

-continued

SPECIMEN 2:
Organism: *Ascaris lumbricoides*
Original sample: 1 *Ascaris lumbricoides* egg per 50 λ aliquot

| Top/Bottom | 295/295 | 295/250 | 295/215 | 250/250 | 250/215 | 215/215 |
|---|---|---|---|---|---|---|
| DEBRIS | 1+/1+ | 1+/1+ | 1+/1+ | 2+/1+ | 3+/2+ | 3+/1+ |

1+ = 25% of filter covered with debris
2+ = 50% of filter covered with debris
3+ = 75% of filter covered with debris
4+ = 100% of filter covered with debris SPECIMEN 3:
Organism: *Diphyllobothrium latum*
Original sample: 1 *Diphyllobothrium latum* egg per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *D. latum* | 0 | 1 | 1 | 1 | 1 | 1 | 0 |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *D. latum* | 0/0 | 0/0 | 0/0 | 0/0 | 0/0 | 0/0 | 0/0 |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | 1+/1+ | 1+/1+ | 1+/1+ | 2+/2+ | 2+/2+ | 3+/2+ |

1+ = 25% of filter covered with debris
2+ = 50% of filter covered with debris
3+ = 75% of filter covered with debris
4+ = 100% of filter covered with debris SPECIMEN 4:
Organism:  *Entamoeba histolytica*
          *Endolimax nana*
          *Blastocystis hominis*
Original sample: 3 *Entamoeba histolytica* cysts per 50 λ aliquot
                5 *Endolimax nana* cysts per 50 λ aliquot
                20 *Blastocystis hominis* per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. histolytica* | 3 | 10 | 7 | 11 | 15 | 17 | 14 |
| *E. nana* | 8 | 23 | 18 | 22 | 26 | 31 | 42 |
| *B. hominis* | 24 | 16 | 14 | 15 | 23 | 30 | 44 |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. histolytica* | 0/2 | 0/0 | 0/0 | 0/0 | 0/0 | 0/0 | 0/0 |
| *E. nana* | 2/4 | 0/0 | 0/0 | 0/0 | 0/0 | 0/0 | 0/0 |
| *B. hominis* | 4/6 | 0/0 | 0/0 | 0/0 | 1/0 | 0/0 | 0/0 |

-continued

SPECIMEN 4:
Organism: *Entamoeba histolytica*
*Endolimax nana*
*Blastocystis hominis*
Original sample: 3 *Entamoeba histolytica* cysts per 50 λ aliquot
5 *Endolimax nana* cysts per 50 λ aliquot
20 *Blastocystis hominis* per 50 λ aliquot Amount of debris on filters:

| FILTER SIZE Top/Bottom | 295/295 | 295/250 | 295/215 | 250/250 | 250/215 | 215/215 |
|---|---|---|---|---|---|---|
| DEBRIS | 1+/1+ | 1+/1+ | 1+/1+ | 1+/1+ | 2+/1+ | 2+/2+ |

1+ = 25% of filter covered with debris
2+ = 50% of filter covered with debris
3+ = 75% of filter covered with debris
4+ = 100% of filter covered with debris SPECIMEN 5:
Organism: *Endolimax nana*
*Blastocystis hominis*
Original sample: 86 *Endolimax nana* cysts per 50 λ aliquot
21 *Blastocystis hominis* per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. Nana* | 88 | NT | NT | NT | 73 | 82 | 92 |
| *B. hominis* | 21 | NT | NT | NT | 25 | 18 | 20 |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. nana* | 0/36 | NT | NT | NT | 0/0 | 3/0 | 4/0 |
| *B. hominis* | 0/15 | NT | NT | NT | 0/0 | 3/0 | 7/0 |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | 2+/1+ | 1+/1+ | 2+/1+ |

1+ = 25% of filter covered with debris
2+ = 50% of filter covered with debris
3+ = 75% of filter covered with debris
4+ = 100% of filter covered with debris SPECIMEN 6:
Organism: *Entamoeba histolytica*
*Blastocystis hominis*
*Endolimax nana*
Original sample: 15 *Entamoeba histolytica* cysts per 50 λ aliquot
58 *Blastocystis hominis* per 50 λ aliquot
25 *Endolimax nana* cysts per 50 λ aliqout Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. histolytica* | 26 | NT | NT | NT | 22 | 30 | 26 |
| *B. hominis* | 48 | NT | NT | NT | 60 | 70 | 75 |
| *E. nana* | 18 | NT | NT | NT | 28 | 32 | 31 |

SPECIMEN 6:
Organism: *Entamoeba histolytica*
*Blastocystis hominis*
*Endolimax nana*
Original sample: 15 *Entamoeba histolytica* cysts per 50 λ aliquot
58 *Blastocystis hominis* per 50 λ aliquot
25 *Endolimax nana* cysts per 50 λ aliqout Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. histolytica* | 0/3 | NT | NT | NT | 0/0 | 0/0 | 0/1 |
| *B. hominis* | 0/2 | NT | NT | NT | 0/0 | 0/0 | 0/3 |
| *E. nana* | 0/5 | NT | NT | NT | 0/0 | 0/0 | 0/2 |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | 2+/1+ | 1+/2+ | 2+/3+ |

1+ = 25% of filter covered with debris
2+ = 50% of filter covered with debris
3+ = 75% of filter covered with debris
4+ = 100% of filter covered with debris

SPECIMEN 7:
Organism: *Entamoeba histolytica*
*Blastocystis hominis*
*Endolimax nana*
Original sample: 3 *Entamoeba histolytica* cysts per 50 λ aliquot
37 *Blastocystis hominis* per 50 λ aliquot
13 *Endolimax nana* cysts per 50 λ aliqout Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. histolytica* | 6 | NT | NT | NT | 4 | 17 | 13 |
| *B. hominis* | 35 | NT | NT | NT | 28 | 36 | 40 |
| *E. nana* | 10 | NT | NT | NT | 31 | 22 | 14 |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. histolytica* | 1/1 | NT | NT | NT | 0/0 | 0/0 | 0/0 |
| *B. hominis* | 2/21 | NT | NT | NT | 0/0 | 0/0 | 0/0 |
| *E. nana* | 0/4 | NT | NT | NT | 0/0 | 0/0 | 0/0 |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | 0/0 | 1+/1+ | 2+/2+ |

1+ = 25% of filter covered with debris
2+ = 50% of filter covered with debris
3+ = 75% of filter covered with debris
4+ = 100% of filter covered with debris SPECIMEN 8:
Organism: *Ascaris lumbricoides*
Original sample: 2 *Ascaris lumbricoides* eggs per 50 λ aliquot
Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *A. lumbricoides* | 10 | NT | NT | NT | 4 | 9 | 10 |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *A. lumbricoides* | 0/2 | NT | NT | NT | 0/0 | 1/0 | 0/0 |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | 1+/0 | 1+/0 | 3+/2+ |

1+ = 25% of filter covered with debris
2+ = 50% of filter covered with debris
3+ = 75% of filter covered with debris
4+ = 100% of filter covered with debris SPECIMEN 9:
Organism: *Strongyloides stercoralis*
Original sample: 0 *Strongyloides stercoralis* larvae per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *S. stercoralis* | 1 | NT | NT | NT | 1 | 2 | 1 |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *S. stercoralis* | 0/0 | NT | NT | NT | 0/0 | 0/0 | 0/0 |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | 0/0 | 1+/0 | 1+/0 |

1+ = 25% of filter covered with debris
2+ = 50% of filter covered with debris
3+ = 75% of filter covered with debris
4+ = 100% of filter covered with debris

SPECIMEN 10:
Organism: *Hymenolepis nana*
Original sample: 3 *Hymenolepis nana* eggs per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *H. nana* | 8 | NT | NT | NT | 35 | 59 | 30 |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *H. nana* | 0/0 | NT | NT | NT | 0/0 | 1/0 | 15/0 |

Amount of debris on filters:

| FILTER SIZE Top/Bottom | | 295/295 | 295/250 | 295/215 | 250/250 | 250/215 | 215/215 |
|---|---|---|---|---|---|---|---|
| DEBRIS | | NT | NT | NT | 0/0 | 1+/2+ | 4+/1+ |

1+ = 25% of filter covered with debris
2+ = 50% of filter covered with debris
3+ = 75% of filter covered with debris
4+ = 100% of filter covered with debris

SPECIMEN 11:
Organism: *Hookworm spp.*
  *Ascaris lumbricoides*
  *Trichuris trichiura*
Original sample: 0 Hookworm spp. eggs per 50 λ aliquot
  49 *Ascaris lumbricoides* eggs per 50 λ aliquot
  3 *Trichuris trichiura* eggs per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| Hockworm spp. | 0 | NT | NT | NT | NT | 1 | NT |
| *A. lumbricoides* | 46 | NT | NT | NT | NT | 66 | NT |
| *T. trichiura* | 3 | NT | NT | NT | NT | 3 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| Hookworm spp. | 0/0 | NT | NT | NT | NT | 0/0 | NT |
| *A. lumbricoides* | 0/0 | NT | NT | NT | NT | 2/1 | NT |
| *T. trichiura* | 0/0 | NT | NT | NT | NT | 0/1 | NT |

Amount of debris on filters:

| FILTER SIZE Top/Bottom | | 295/295 | 295/250 | 295/215 | 250/250 | 250/215 | 215/215 |
|---|---|---|---|---|---|---|---|
| DEBRIS | | NT | NT | NT | NT | 2+/1+ | NT |

1+ = 25% of filter covered with debris
2+ = 50% of filter covered with debris
3+ = 75% of filter covered with debris
4+ = 100% of filter covered with debris SPECIMEN 12:
Organism: *Trichuris trichiura*
　　　　　  *Enterobius vermicularis*
Original sample:　0 *Trichuris trichiura* eggs per 50 λ aliquot
　　　　　　　　  1 *Enterobius vermicularis* egg per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *T. trichiura* | 0 | NT | NT | NT | NT | 1 | NT |
| *E. vermicularis* | 6 | NT | NT | NT | NT | 4 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *T. trichiura* | 0/0 | NT | NT | NT | NT | 0/0 | NT |
| *E. vermicularis* | 0/0 | NT | NT | NT | NT | 0/0 | NT |

Amount of debris on filters:

| FILTER SIZE TOP/Bottom | 295/295 | 295/250 | 295/215 | 250/250 | 250/215 | 215/215 |
|---|---|---|---|---|---|---|
| DEBRIS | NT | NT | NT | NT | 1+/0 | NT |

1+ = 25% of filter covered with debris
2+ = 50% of filter covered with debris
3+ = 75% of filter covered with debris
4+ = 100% of filter covered with debris SPECIMEN 13:
Organism: *Hymenolepis nana*
　　　　　  *Giardia lamblia*
　　　　　  *Endolimax nana*
Original sample:　5 *Hymenolepis nana* eggs per 50 λ aliquot
　　　　　　　　 23 *Giardia lamblia* cysts per 50 λ aliquot
　　　　　　　　 11 *Endolimax nana* cysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *H. nana* | 2 | NT | NT | NT | NT | 5 | NT |
| *G. lamblia* | 33 | NT | NT | NT | NT | 39 | NT |
| *E. nana* | 42 | NT | NT | NT | NT | 27 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *H. nana* | 0/0 | NT | NT | NT | NT | 0/0 | NT |
| *G. lamblia* | 0/0 | NT | NT | NT | NT | 0/0 | NT |
| *E. nana* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 1+/1+ | NT |

1+ = 25% of filter covered with debris
2+ = 50% of filter covered with debris
3+ = 75% of filter covered with debris
4+ = 100% of filter covered with debris SPECIMEN 14:
Organism: *Trichuris trichiura*
*Strongyloides stercoralis*
Hookworm spp.
Original sample: 0 *Trichuris trichiura* eggs per 50 λ aliquot
13 *Strongyloides stercoralis* larvae per 50 λ aliquot
8 Hookworm spp. eggs per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *T. trichiura* | 0 | NT | NT | NT | NT | 1 | NT |
| *S. stercoralis* | 30 | NT | NT | NT | NT | 23 | NT |
| Hookworm spp. | 2 | NT | NT | NT | NT | 7 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *T. trichiura* | 0/0 | NT | NT | NT | NT | 0/0 | NT |
| *S. stercoralis* | 0/0 | NT | NT | NT | NT | 1/2 | NT |
| Hookworm spp. | 0/0 | NT | NT | NT | NT | 0/1 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/1+ | NT |

1+ = 25% of filter covered with debris
2+ = 50% of filter covered with debris
3+ = 75% of filter covered with debris
4+ = 100% of filter covered with debris SPECIMEN 15:
Organism: *Diphyllobothrium latum*
*Taenia spp.*
Original sample: 1 *Diphyllobothrium latum* egg per 50 λ alliquot
1 *Taenia spp.* egg per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *D. latum* | 9 | NT | NT | NT | NT | 5 | NT |
| *Taenia spp.* | 5 | NT | NT | NT | NT | 9 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *D. latum* | 0/0 | NT | NT | NT | NT | 1/1 | NT |
| *Taenia spp.* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 1+/0 | NT |

1+ = 25% of filter covered with debris
2+ = 50% of filter covered with debris
3+ = 75% of filter covered with debris
4+ = 100% of filter covered with debris SPECIMEN 16:
Organism: *Schistosoma mansoni*
*Ascaris lumbricoides*
*Entamoeba coli*
Hookworm spp.
Original sample: 5 *Schistosoma mansoni* eggs per 50 λ aliquot
6 *Ascaris lumbricoides* eggs per 50 λ aliquot
24 *Entamoeba coli* cysts per 50 λ aliquot
1 Hookworm spp. egg per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *S. mansoni* | 4 | NT | NT | NT | NT | 4 | 0 |
| *A. lumbricoides* | 8 | NT | NT | NT | NT | 2 | NT |
| *E. coli* | 22 | NT | NT | NT | NT | 38 | NT |
| Hookworm spp. | 2 | NT | NT | NT | NT | 1 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *S. mansoni* | 0/0 | NT | NT | NT | NT | 0/0 | NT |
| *A. lumbricoides* | 0/0 | NT | NT | NT | NT | 0/0 | NT |
| *E. coli* | 0/0 | NT | NT | NT | NT | 0/0 | NT |
| Hookworm spp. | 0/0 | NT | NT | NT | NT | 0/0 | NT |

Amount of debris on filters:

| FILTER SIZE Top/Bottom | 295/295 | 295/250 | 295/215 | 256/250 | 250/215 | 215/215 |
|---|---|---|---|---|---|---|
| DEBRIS | NT | NT | NT | NT | 4+/1+ | NT |

1+ = 25% of filter covered with debris
2+ = 50% of filter covered with debris
3+ = 75% of filter covered with debris
4+ = 100% of filter covered with debris SPECIMEN 17:
Organism: *Endolimax nana*
Original sample: 17 *Endolimax nana* cysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. nana* | 21 | NT | NT | NT | NT | 26 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. nana* | 0/6 | NT | NT | NT | NT | 0/2 | NT |

-continued

SPECIMEN 17:
Organism: *Endolimax nana*
Original sample: 17 *Endolimax nana* cysts per 50 λ aliquot Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 1+/1+ | NT |

1+ = 25% of filter covered with debris
2+ = 50% of filter covered with debris
3+ = 75% of filter covered with debris
4+ = 100% of filter covered with debris SPECIMEN 18:
Organism: *Entamoeba coli*
 *Endolimax nana*
 *Iodamoeba bütschlii*
 *Trichuris trichiura*
Original sample: 19 *Entamoeba coli* cysts per 50 λ aliquot
 36 *Endolimax nana* cysts per 50 λ aliquot
 28 *Iodamoeba bütschlii* cysts per 50 λ aliquot
 3 *Tricuris trichiura* eggs per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. coli* | 26 | NT | NT | NT | NT | 37 | NT |
| *E. nana* | 44 | NT | NT | NT | NT | 39 | NT |
| *I. bütschlii* | 26 | NT | NT | NT | NT | 32 | NT |
| *T. trichiura* | 5 | NT | NT | NT | NT | 3 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. coli* | 0/3 | NT | NT | NT | NT | 2/0 | NT |
| *E. nana* | 0/0 | NT | NT | NT | NT | 0/1 | NT |
| *I. bütschlii* | 0/4 | NT | NT | NT | NT | 1/1 | NT |
| *T. trichiura* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/1+ | NT |

1+ = 25% of filter covered with debris
2+ = 50% of filter covered with debris
3+ = 75% of filter covered with debris
4+ = 100% of filter covered with debris SPECIMEN 19:
Organism: *Ascaris lumbricoides*
 *Endolimax nana*
Original Sample: 1 *Ascaris lumbricoides* egg per 50 λ aliquot
 22 *Endolimax nana* cysts per 50 λ aliquot Concentration Sediment:
(organisms per 50 λ aliquot)

| ORGANISM | O&P | 295/295 | 295/250 | 250/215 | 250/250 | 250/215 | 215/215 |
|---|---|---|---|---|---|---|---|
| *A. lumbricoides* | 10 | NT | NT | NT | NT | 14 | NT |
| *A. nana* | 37 | NT | NT | NT | NT | 35 | NT |

SPECIMEN 19:
Organism: *Ascaris lumbricoides*
          *Endolimax nana*
Original Sample: 1 *Ascaris lumbricoides* egg per 50 λ aliquot
                22 *Endolimax nana* cysts per 50 λ aliquot Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *A. lumbricoides* | 0/0 | NT | NT | NT | NT | 0/0 | NT |
| *E. nana* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 1+/1+ | NT |

1+ = 25% of filter covered with debris
2+ = 50% of filter covered with debris
3+ = 75% of filter covered with debris
4+ = 100% of filter covered with debris SPECIMEN 20:
Organism: *Entamoeba coli*
          *Entamoeba hartmanni*
          *Blastocystis hominis*
Original sample: 20 *Entamoeba coli* cysts per 50 λ aliquot
              14 *Entamoeba hartmanni* cysts per 50 λ aliquot
              34 *Blastocystis hominis* eggs per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. coli* | 25 | NT | NT | NT | NT | 30 | NT |
| *E. hartmanni* | 11 | NT | NT | NT | NT | 16 | NT |
| *B. hominis* | 51 | NT | NT | NT | NT | 66 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. coli* | 1/4 | NT | NT | NT | NT | 0/0 | NT |
| *E. hartmanni* | 0/2 | NT | NT | NT | NT | 0/3 | NT |
| *b. hominis* | 0/8 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/2+ | NT |

1+ = 25% of filter covered with debris
2+ = 50% of filter covered with debris
3+ = 75% of filter covered with debris
4+ = 100% of filter covered with debris SPECIMEN 21:
Organism:   *Iodamoeba bütschlii*
            *Entamoeba hartmanni*
Original sample:   7 *Iodamoeba bütschlii* cysts per 50 λ aliquot
                   4 *Entamoeba hartmanni* cysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *I. bütschlii* | 9 | NT | NT | NT | NT | 13 | NT |
| *E. hartmanni* | 11 | NT | NT | NT | NT | 10 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *I. bütschlii* | 0/0 | NT | NT | NT | NT | 0/0 | NT |
| *E. hartmanni* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 1+/0 | NT |

1+ = 25% of filter covered with debris
2+ = 50% of filter covered with debris
3+ = 75% of filter covered with debris
4+ = 100% of filter covered with debris SPECIMEN 22:
Organism:   *Trichuris trichiura*
            *Entamoeba hartmanni*
Original sample:   1 *Trichuris trichiura* egg per 50 λ aliquot
                   3 *Entamoeba hartmanni* cysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *T. trichiura* | 4 | NT | NT | NT | NT | 7 | NT |
| *E. hartmanni* | 5 | NT | NT | NT | NT | 11 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *T. trichiura* | 0/0 | NT | NT | NT | NT | 0/0 | NT |
| *E. hartmanni* | 0/8 | NT | NT | NT | NT | 2/1 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/1+ | NT |

1+ = 25% of filter covered with debris
2+ = 50% of filter covered with debris
3+ = 75% of filter covered with debris
4+ = 100% of filter covered with debris

SPECIMEN 23:
Organism:
*Trichuris trichiura*
*Entamoeba coli*
Original sample:
1 *Trichuris trichiura* egg per 50 λ aliquot
3 *Entamoeba coli* cysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *T. trichiura* | 1 | NT | NT | NT | NT | 4 | NT |
| *E. coli* | 16 | NT | NT | NT | NT | 24 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *T. trichiura* | 0/0 | NT | NT | NT | NT | 0/0 | NT |
| *E. coli* | 0/3 | NT | NT | NT | NT | 0/5 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/1+ | NT |

1+ = 25% of filter covered with debris
2+ = 50% of filter covered with debris
3+ = 75% of filter covered with debris
4+ = 100% of filter covered with debris

SPECIMEN 24:
Organism:
*Trichuris trichiura*
*Entamoeba hartmanni*
Original sample:
1 *Trichuris trichiura* egg per 50 λ aliquot
11 *Entamoeba hartmanni* cysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *T. trichiura* | 6 | NT | NT | NT | NT | 6 | NT |
| *E. hartmanni* | 21 | NT | NT | NT | NT | 34 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *T. trichiura* | 0/0 | NT | NT | NT | NT | 0/0 | NT |
| *E. hartmanni* | 0/4 | NT | NT | NT | NT | 0/1 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 3+/1+ | NT |

1+ = 25% of filter covered with debris
2+ = 50% of filter covered with debris
3+ = 75% of filter covered with debris
4+ = 100% of filter covered with debris SPECIMEN 25:
Organism:
*Trichuris trichiura*
*Endolimax nana*
Original sample:
2 *Trichuris trichiura* eggs per 50 λ aliquot
38 *Endolimax nana* cysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *T. trichiura* | 9 | NT | NT | NT | NT | 7 | NT |
| *E. nana* | 51 | NT | NT | NT | NT | 66 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *T. trichiura* | 0/0 | NT | NT | NT | NT | 0/0 | NT |
| *E. nana* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 1+/0 | NT |

1+ = 25% of filter covered with debris
2+ = 50% of filter covered with debris
3+ = 75% of filter covered with debris
4+ = 100% of filter covered with debris SPECIMEN 26:
Organism:
*Entamoeba hartmanni*
*Endolimax nana*
*Ascaris lumbricoides*
*Trichuris trichiura*
Original sample:
10 *Entamoeba hartmanni* cysts per 50 λ aliquot
6 *Endolimax nana* cysts per 50 λ aliquot
8 *Ascaris lumbricoides* eggs per 50 λ aliquot
3 *Trichuris trichiura* eggs per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *E. hartmanni* | 21 | NT | NT | NT | NT | 27 | NT |
| *E. nana* | 13 | NT | NT | NT | NT | 20 | NT |
| *A. lumbricoides* | 11 | NT | NT | NT | NT | 13 | NT |
| *T. trichiura* | 5 | NT | NT | NT | NT | 4 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *E. hartmanni* | 0/6 | NT | NT | NT | NT | 1/3 | NT |
| *E. nana* | 0/3 | NT | NT | NT | NT | 0/0 | NT |
| *A. lumbricoides* | 0/1 | NT | NT | NT | NT | 0/0 | NT |
| *T. trichiura* | 0/0 | NT | NT | NT | NT | 0/0 | NT |

SPECIMEN 26:
Organism:
*Entamoeba hartmanni*
*Endolimax nana*
*Ascaris lumbricoides*
*Trichuris trichiura*
Original sample:
10 *Entamoeba hartmanni* cysts per 50 λ aliquot
6 *Endolimax nana* cysts per 50 λ aliquot
8 *Ascaris lumbricoides* eggs per 50 λ aliquot
3 *Trichuris trichiura* eggs per 50 λ aliquot Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/1+ | NT |

1+ = 25% of filter covered with debris
2+ = 50% of filter covered with debris
3+ = 75% of filter covered with debris
4+ = 100% of filter covered with debris

SPECIMEN 27:
Organism:
*Giardia lamblia*
Original sample:
11 *Giardia lamblia* cysts and trophozoites per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *G. lamblia* | 25 | NT | NT | NT | NT | 33 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *G. lamblia* | 0/6 | NT | NT | NT | NT | 0/2 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 3+/2+ | NT |

1+ = 25% of filter covered with debris
2+ = 50% of filter covered with debris
3+ = 75% of filter covered with debris
4+ = 100% of filter covered with debris

SPECIMEN 28:
Organism:
*Ascaris lumbricoides*
Original sample:
8 *Ascaris lumbricoides* eggs per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *A. lumbricoides* | 13 | NT | NT | NT | NT | 11 | NT |

SPECIMEN 28:
Organism:
*Ascaris lumbricoides*
Original sample:
8 *Ascaris lumbricoides* eggs per 50 λ aliquot Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *A. lumbricoides* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/1+ | NT |

1+ = 25% of filter covered with debris
2+ = 50% of filter covered with debris
3+ = 75% of filter covered with debris
4+ = 100% of filter covered with debris SPECIMEN 29:
Organism:
*Iodamoeba bütschlii*
*Entamoeba coli*
*Entamoeba hartmanni*
*Blastocystis hominis*
Original sample:
7 *Iodamoeba bütschlii* cysts per 50 λ aliquot
19 *Entamoeba coli* cysts per 50 λ aliquot
15 *Entamoeba hartmanni* cysts per 50 λ aliquot
15 *Blastocystis hominis* per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| *I. bütschlii* | 23 | NT | NT | NT | NT | 35 | NT |
| *E. coli* | 37 | NT | NT | NT | NT | 29 | NT |
| *E. hartmanni* | 22 | NT | NT | NT | NT | 33 | NT |
| *B. hominis* | 25 | NT | NT | NT | NT | 41 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| *I. bütschlii* | 0/0 | NT | NT | NT | NT | 0/0 | NT |
| *E. coli* | 0/0 | NT | NT | NT | NT | 0/2 | NT |
| *E. hartmanni* | 0/2 | NT | NT | NT | NT | 0/0 | NT |
| *B. hominis* | 0/0 | NT | NT | NT | NT | 0/0 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/2+ | NT |

1+ = 25% of filter covered with debris
2+ = 50% of filter covered with debris
3+ = 75% of filter covered with debris
4+ = 100% of filter covered with debris SPECIMEN 30:
Organism:
Crypstosporidium sp.
Original sample:
6 Cryptosporidium sp. oocysts per 50 λ aliquot Concentration Sediment:
(organisms per 50 λ aliquot)

| ORGANISM | O&P | 295/295 | 295/250 | 295/215 | 250/250 | 250/215 | 215/215 |
|---|---|---|---|---|---|---|---|
| Cryptosporidium | 31 | NT | NT | NT | NT | 39 | NT |

Organisms Lost:
(organisms per 50 λ aliquot)

| ORGANISM | O&P wash/debris plug | 295/295 | 295/250 | 295/215 | 250/250 | 250/215 | 215/215 |
|---|---|---|---|---|---|---|---|
| Cryptosporidium | 0/9 | NT | NT | NT | NT | 1/4 | NT |

Amount of debris on filters:

| FILTER SIZE Top/Bottom | 295/295 | 295/250 | 295/215 | 250/250 | 250/215 | 215/215 |
|---|---|---|---|---|---|---|
| DEBRIS | NT | NT | NT | NT | 2+/1+ | NT |

1+ = 25% of filter covered with debris
2+ = 50% of filter covered with debris
3+ = 75% of filter covered with debris
4+ = 100% of filter covered with debris

DATA SUMMARY

| Organism | Original Sample | Total Number of Organisms Detected O&P | Filter System | Total Number of Organisms Lost O&P | Filter System |
|---|---|---|---|---|---|
| A. lumbricoides | 75 | 116 | 180 | 3 | 6 |
| B. hominis | 188 | 204 | 261 | 58 | 3 |
| Cryptosporidium | 6 | 31 | 39 | 9 | 5 |
| D. latum | 3 | 14 | 14 | 0 | 2 |
| E. nana | 259 | 332 | 380 | 60 | 6 |
| E. coli | 85 | 126 | 158 | 11 | 9 |
| E. hartmanni | 57 | 91 | 131 | 22 | 11 |
| E. histolytica | 21 | 35 | 64 | 7 | 0 |
| E. vermicularis | 1 | 6 | 4 | 0 | 0 |
| G. lamblia | 34 | 58 | 72 | 6 | 2 |
| Hookworm | 9 | 4 | 9 | 0 | 1 |
| H. nana | 8 | 10 | 64 | 0 | 1 |
| I. bütschlii | 42 | 58 | 80 | 4 | 2 |
| S. mansoni | 5 | 4 | 4 | 0 | 0 |
| S. stercoralis | 13 | 31 | 25 | 0 | 0 |
| Taenia | 1 | 5 | 9 | 0 | 0 |
| T. trichiura | 14 | 33 | 36 | 0 | 1 |
|  | 821 | 1158 | 1530 | 180 | 49 |

While the present invention has been described and illustrated in conjunction with a number of specific embodiments, those skilled in the art will appreciate that variations and modifications may be made without departing from the principles of the invention as herein illustrated, described and claimed.

The invention may be embodied in other specific forms without departing from the spirit or essential characteristics thereof. The present embodiments are to be considered in all respects as illustrative, and not restrictive. The scope of the invention, is therefore, indicated by the appended claims rather than by the foregoing description, and all changes which come within the meaning and range of equivalency of the claims are to be embraced within their scope.

I claim:

1. A filtration apparatus for analyzing human or animal specimens, comprising:

a specimen receptacle having a filter holder section-joining end;

a filter holder section having a specimen receptacle-joining end and a collection receptacle-joining end, said specimen receptacle-joining end being in fluid communication with said filter holder section-joining end of said specimen receptacle;

a collection receptacle having a filter holder section-joining end and a closed end, said filter holder section-joining end of said collection receptacle being in fluid communication with said collection receptacle-joining end of said filter holder section;

a coarse filter having an average pore size within the range of about 180 to about 295 micrometers, said coarse filter being attached to said filter holder section;

a fine filter having an average pore size within the range of about 180 to about 295 micrometers, said fine filter being attached to said filter holder section;

wherein the average pore size of said coarse filter is greater the average pore size of said fine filter;

wherein said coarse filter is attached proximally to said specimen receptacle-joining end and said fine filter is attached distally to said specimen receptacle-joining end;

wherein said coarse and fine filters provide fluid communication between said specimen receptacle and said collection receptacle; and whereby said apparatus is effective for the centrifugal separation of ova and parasites from specimens by retaining contaminating material on said coarse and fine filters so that the ova and parasites form a pellet, which is substantially free of contaminating material, in said closed end of said collection receptacle.

2. An apparatus according to claim 1, further comprising at least one filter attachment mechanism.

3. An apparatus according to claim 1, further comprising a filter support mechanism.

4. An apparatus according to claim 1, wherein the average pore size of said coarse filter is within the range of about 210 to about 295 micrometers.

5. An apparatus according to claim 4, wherein the average pore size of said coarse filter is about 250 micrometers.

6. An apparatus according to claim 1, wherein the average pore size of said fine filter is within the range of about 180 to about 250 micrometers.

7. An apparatus according to claim 6, wherein the average pore size of said fine filter is about 210 micrometers.

8. An apparatus according to claim 1, wherein said coarse filter and said fine filter are independently selected from the group comprising teflon, nylon, polypropylene, polyethylene, nitrocellulose, stainless steel, copper and nickel.

9. An apparatus according to claim 8, wherein said coarse and fine filters comprise stainless steel.

10. An apparatus according to claim 1, wherein said coarse filter and said fine filter further comprise a cartridge.

11. An apparatus according to claim 1, wherein said filter holder section-joining end of said specimen receptacle is integral with said specimen receptacle-joining end of said filter holder section.

12. An apparatus according to claim 1, wherein said filter holder section is separable from said specimen receptacle.

13. An apparatus according to claim 1, wherein said collection receptacle is separable from said filter holder section.

14. An apparatus according to claim 1, further comprising a cap; wherein said specimen receptacle further comprises a cap-receiving end.

15. An apparatus according to claim 1, wherein said specimen receptacle further comprises a reservoir having a cap-receiving end, and a cap having a reservoir receiving end; wherein said cap sealingly engages said cap-receiving end of said reservoir.

16. A method for centrifugally separating ova and parasites from specimens, comprising:
 (a) mixing a specimen with a preservation solution to form a mixture;
 (b) transferring said mixture a specimen receptacle of a filtration apparatus, said filtration apparatus comprising:
  a specimen receptacle having a filter holder section-joining end;
  a filter holder section having a specimen receptacle-joining end and a collection receptacle-joining end, said specimen receptacle-joining end being in fluid communication with said filter holder section-joining end of said specimen receptacle;
  a collection receptacle having a filter holder section-joining end and a closed end, said filter holder section-joining end of said collection receptacle being in fluid communication with said collection receptacle-joining end of said filter holder section;
  a coarse filter having an average pore size within the range of about 180 to about 295 micrometers, said coarse filter being attached to said filter holder section;
  a fine filter having an average pore size within the range of about 180 to about 295 micrometers, said fine filter being attached to said filter holder section;
  wherein the average pore size of said coarse filter is greater than the average pore size of said fine filter;
  wherein said coarse filter is attached proximally to said specimen receptacle joining end and said fine filter is attached distally to said specimen receptacle joining end; and
  whereby said coarse and fine filters provide fluid communication between said specimen receptacle and said collection receptacle;
 (c) centrifuging said filtration apparatus to produce a supernatant and a pellet in said collection receptacle;
  whereby contaminating material is retained on said fine and coarse filters and said pellet is substantially free of contaminating material.

17. A method according to claim 16, further comprising examining said pellet for the presence of ova and parasites.

18. A method according to claim 16, further comprising pre-filtering said mixture before transferring said mixture to said specimen receptacle.

19. A method according to claim 16, further comprising washing said mixture.

20. A method according to claim 16, wherein said specimen is selected from the group consisting of human specimens and animal specimens.

21. A method according to claim 20, wherein said human specimen is selected from the group consisting of fecal material, gastric aspirates, duodenal aspirates and sputum.

22. A method according to claim 21, wherein said human specimen is fecal material.

23. A method according to claim 16, wherein said mixing of said specimen with said preservation solution occurs in a preservation solution dispenser.

24. A method according to claim 16, wherein said preservation solution is selected from the group consisting of 5% buffered formalin, 10% buffered formalin, 37% aqueous neutral formalin, ECO-SAFE and PARA-SAFE, cupric polyvinylalcohol, zinc polyvinyl alcohol, mercuric polyvinyl alcohol, sodium acetic formaldehyde, methiolate-iodine-formaldehyde, CON-SED and PROTO-FIX.

25. A kit for detecting the presence of ova and parasites in specimens, comprising:
 (a) a preservation solution dispenser, said dispenser containing a preservation solution; and
 (b) a filtration apparatus, said filtration apparatus comprising:
  a specimen receptacle having a filter holder section-joining end;
  a filter holder section having a specimen receptacle-joining end and a collection receptacle-joining end, said specimen receptacle-joining end being in fluid communication with said filter holder section-joining end of said specimen receptacle;

a collection receptacle having a filter holder section-joining end, said filter holder section-joining end of said collection receptacle being in fluid communication with said collection receptacle-joining end of said filter holder section;

a coarse filter having an average pore size within the range of about 180 to about 295 micrometers, said coarse filter being attached to said filter holder section;

a fine filter having an average pore size within the range of about 180 to about 295 micrometers, said fine filter being attached to said filter holder section;

wherein the average pore size of said coarse filter is greater than or equal to the average pore size of said fine filter;

wherein said coarse filter is attached proximally to said specimen receptacle joining end and said fine filter is attached distally to said specimen receptacle joining end;

whereby said coarse and fine filters provide fluid communication between said specimen receptacle and said collection receptacle; and whereby said apparatus is effective for the centrifugal separation of ova and parasites from specimens by retaining contaminating material on said coarse and fine filters so that the ova and parasites form a pellet, which is substantially free of contaminating material, in said closed end of said collection receptacle.

26. A kit according to claim 25, wherein said dispenser has a specimen receptacle-receiving end, said specimen receptacle-joining end of said dispenser being adapted to sealingly engage said filter holder section-joining end of said specimen receptacle.

27. A kit according to claim 26, wherein said specimen receptacle-joining end of said dispenser is a sleeve.

28. A kit according to claim 26, wherein said specimen receptacle-joining end of said dispenser is an engagement ring.

29. A kit according to claim 25, further comprising a specimen-transferring device.

30. A kit according to claim 25, wherein said preservation solution dispenser further comprises tab and removable portion.

31. A kit according to claim 25, further comprising a macro-filter.

32. A kit according to claim 31, wherein said preservation solution dispenser further comprises a macro-filter.

33. A kit according to claim 31, wherein said macro-filter is selected from the group consisting of funnels and cartridges.

34. A kit according to claim 19, wherein said preservation solution dispenser contains a preservation solution selected from the group consisting of 5% buffered formalin, 10% buffered formalin, 37% aqueous neutral formalin, ECO-SAFE and PARA-SAFE, cupric polyvinylalcohol, zinc polyvinyl alcohol, mercuric polyvinyl alcohol, sodium acetic formaldehyde, methiolate-iodine-formaldehyde, CONSED and PROTO-FIX.

* * * * *